United States Patent [19]

Halls et al.

[11] Patent Number: 4,784,157

[45] Date of Patent: Nov. 15, 1988

[54] METHOD AND APPARATUS FOR TAKING SAMPLES FROM OR ADMINISTERING MEDICATION TO A PATIENT

[76] Inventors: Justin A. T. Halls, 147 Briar Road, Kingswood, Garston, Watford, Herts; David W. Hawes, 40 Leighfield, Mortimer, Reading, Berks; Heinz S. Wolff, 53 Meadway, London NW11; Richard D. Vahrman, 20 First Avenue, Garston, Watford, Herts, all of England

[21] Appl. No.: 7,678

[22] Filed: Jan. 28, 1987

[30] Foreign Application Priority Data

Feb. 4, 1986 [GB] United Kingdom ............... 8602732

[51] Int. Cl.$^4$ ................................................ A61B 5/00
[52] U.S. Cl. .................................. 128/762; 604/66; 604/191
[58] Field of Search ........................... 128/762–766; 604/28, 35, 36, 38, 51, 52, 53, 151, 66, 191, 246

[56] References Cited

U.S. PATENT DOCUMENTS

| | | | |
|---|---|---|---|
| 3,043,303 | 7/1962 | Still | 604/66 |
| 3,405,706 | 10/1968 | Cinqualbre | 128/764 |
| 3,494,351 | 2/1970 | Horn | 604/191 |
| 3,616,789 | 11/1971 | Grabhorn | 128/762 |
| 3,633,566 | 1/1972 | Grabhorn | 128/762 |
| 3,674,011 | 7/1972 | Michel et al. | 128/762 |
| 4,077,395 | 3/1978 | Abolner | 128/762 |
| 4,246,899 | 1/1981 | Loseff | 128/764 |
| 4,385,630 | 5/1983 | Gilcher et al. | 604/35 |
| 4,657,027 | 4/1986 | Paulsen | 128/762 |

FOREIGN PATENT DOCUMENTS 0107579 5/1984 European Pat. Off. ........... 128/762

*Primary Examiner*—Max Hindenburg
*Attorney, Agent, or Firm*—Cohen, Pontani & Lieberman

[57] ABSTRACT

A controlled apparatus for withdrawing fluids from a patient or for administering medication to a patient, or both, which controlled apparatus may be remotely and/or automatically controlled. The apparatus includes a manifold and cannula for connecting the manifold to a patient, one or more syringes connected to the manifold, a pump for pumping liquid into and out of the manifold and a controller for controlling the operation of the syringes and the pump. A method of using the apparatus is also provided.

The controlled apparatus is especially useful for the programmed withdrawal of blood from a blood vessel of a patient.

20 Claims, 3 Drawing Sheets

METHOD AND APPARATUS FOR TAKING SAMPLES FROM OR ADMINISTERING MEDICATION TO A PATIENT

BACKGROUND OF THE INVENTION

This invention relates to a method and apparatus for taking samples from or administering medication to a patient, and, in a preferred form, for the continuous monitoring of a given physiological condition of an ambulatory patient.

One form of the invention is concerned simply with taking a sample from a patient without the presence of a qualified attendant, for example at a given hour of the night. A more developed form of the invention is concerned with continuous monitoring.

The continuous monitoring of certain physiological parameters in patients who are going about their normal lives has been an important advance in diagnostics over the last fifteen years. Knowledge of the effect of the stresses of actual living on for example the patient's ECG or EEG has added greatly to the clinician's capacity to understand the patient's illness and prescribe appropriate drugs.

However, it has not been possible for the clinician to follow the concentration of these drugs in the patient's blood, and relate it in detail to the changes produced in for example heart or brain action. To date, there has been no effective means of withdrawing on a regular basis a plurality of discrete samples of blood from the ambulatory patient.

Hitherto efforts have been made to draw off a sample of blood continuously, either for testing continuously or for separation into aliquots for testing. However, trouble arises over blocking of the cannula by blood clots, and the simultaneous administration of an anticoagulant has not proved feasible at the low flow rates required for an ambulatory device.

The same problems arise if it is required to take a single sample at a given time when no attendance can be provided.

BRIEF SUMMARY OF THE INVENTION

The approach of the present invention in its broad aspect is to collect a discrete sample of blood or other fluid straight into an individual container: before and after sampling the whole system is emptied and flushed through, so that there is no opportunity for clotting to occur.

The invention in one aspect accordingly provides apparatus for taking a blood sample comprising a syringe for drawing a blood sample from a manifold to be connected with the patient, and fluid flow means to draw blood into the manifold before sampling and to flush it afterwards with anticoagulant liquid.

Preferably the fluid flow means includes a reservoir for anticoagulant liquid and a reversible pump therefor, and control means for the pump and syringe, whereby the pump:

(a) before sampling, pumps anticoagulant liquid slowly into the patient;

(b) for sampling, pumps blood rapidly into the manifold;

(c) after sampling, flushes the manifold rapidly with anticoagulant liquid; and thereafter (d) again pumps anticoagulant liquid slowly into the In a further aspect the invention provides a method of taking a blood sample from an ambulatory subject comprising:

connecting a manifold to the patient, activating a syringe to draw a sample from the manifold, and drawing blood from the patient into the manifold before sampling and flushing it afterwards with anticoagulant liquid.

Preferably, in the method just described, before and after sampling, anticoagulant liquid is pumped slowly into the patient; immediately before sampling blood is drawn rapidly from the vein into the manifold; immediately after sampling anticoagulant liquid is pumped into the manifold to displace the blood; and thereafter anticoagulant liquid is again pumped slowly into the subject.

For continuous monitoring of an ambulatory patient, means is provided to be carried on the patient, including a series of syringes for successively drawing blood samples from the manifold, the previously mentioned fluid flow means comprising reservoir and pump, and control means for the syringes and pump.

The pack may also include means to inject medication into the patient, which may be done in addition to or in lieu of blood sampling.

By way of example only, there may be a bank of say seven syringes which are operated successively at one hour intervals. The apparatus may be small enough to be attached to a patient's arm for periods up to a day.

BRIEF DESCRIPTION OF THE DRAWINGS

In the drawings:

FIG. 3 is a sketch illustrating the pack carried by the

DETAILED DESCRIPTION OF PREFERRED EMBODIMENT

Figure 1:
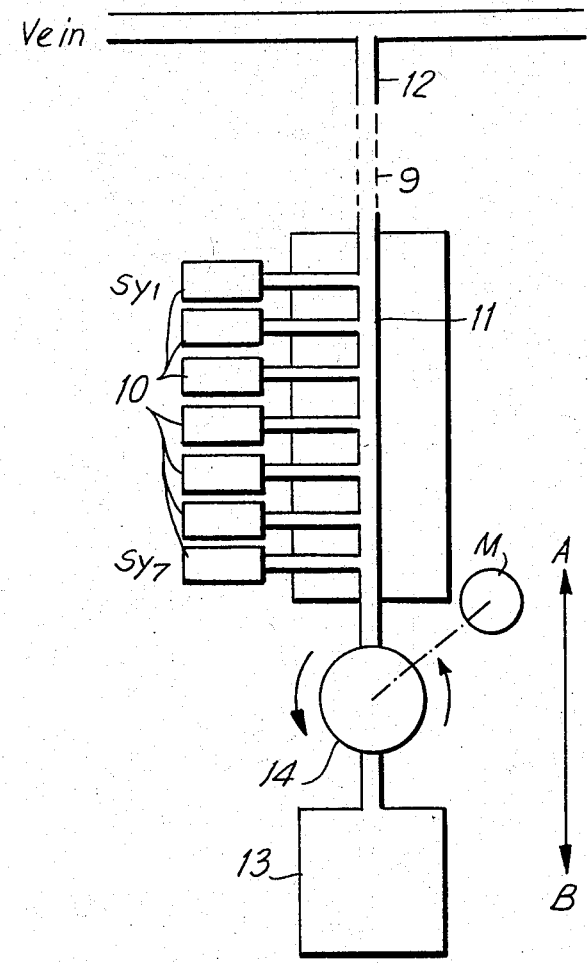
FIG. 1 is a diagram to illustrate the construction and method of use of a blood sampling pack embodying this invention.

Referring now to FIG. 1 in detail, a series of syringes 10 are connected to a manifold 11 which itself is connected at one end preferably by a flexible tube 9, (shown in dotted line) to a cannula 12 inserted into a vein of a patient. At the opposite end the manifold 11 is connected to a reservoir 13 of heparinised saline through a peristaltic pump 14 driven by a reversible electric motor M.

There are seven syringes 10 shown in FIG. 1. Clearly the number may be greater or smaller depending on requirements. As will be explained, the invention envisages within its scope a construction with only one syringe. While the syringes may be of any construction, each syringe is preferably constructed as described in U.S. patent application Ser. No. 007,730 filed on Jan. 28, 1987 by Heinz Siegfried Wolff and David William Hawes, for SYRINGE, the contents of which are hereby incorporated by reference.

The timing of the successive operations is preferably controlled by a microprocessor (not shown in FIG. 1) which is programmed by a key-pad (also not shown) plugged in for the purpose. Of course, other controllers may be used in lieu of a microprocessor. In general a routine program suffices, but if necessary the program can be adjusted by the investigator in charge. Typical values for a satisfactory operation are as follows:

(1) Between samples the pump 14 runs slowly in direction A and pumps herparinised saline into the vein at a rate of 2 ml/hr, to prevent the cannula from becoming occluded by clotted blood.

(2) Immediately prior to sampling at preselected intervals the pump 14 runs fast (about ten times the perfusion speed) in direction B, filling the catheter C and the manifold 11 with blood. After a period of time or number of revolutions sufficient to take the end of the blood column well past the manifold, the pump stops. Alternatively, a light sensitive device or other blood sensing means may be employed to stop the pump motor on sensing blood at a given point beyond the manifold 11.

(3) The first syringe 10 Syl operates and aspirates blood from the manifold 11 and via cannula 12 from the vein. Preferably, it stops aspirating slightly before the syringe chamber is full. This is easily accomplished if using the aforementioned Wolff et al syringe structure.

(4) Immediately after sampling by syringe Syl, the pump 14 again reverses direction, and at high speed flushes the connecting tube 9 and cannula 12 with fresh heparinised saline drawn from reservoir 13 back into the patient's vein V.

(5) Syringe Syl is reactuated, drawing in a small amount of the heparinised saline with which the manifold is now filled. This aspiration results in syringe Syl now being filled, primarily with the patient's blood to which has been added a small amount of heparinized saline to prevent clotting in syringe Syl.

(6) The system then reverts to the original condition described under (1) above. In one typical program, at preselected intervals steps 1 to 6 above will be repeated for each syringe 10.

The method and apparatus described has the following advantages:

(a) Because the blood is held only briefly in the manifold and then immediately flushed out with heparinised saline, there is no time for the blood to clot. This means not only that there is no risk of the system becoming blocked and ceasing to run but, more important, there is no risk to the patient from embolism.

(b) In the system as illustrated, up to seven samples can be taken without further attention, and further series of seven samples can be taken simply by inserting a new syringe unit. The catheter does not need to be changed for several days.

Since for most purposes hourly samples are adequate, this means that the patient does not have to return for attention for seven hours. If less frequent sampling is acceptable, or if more syringes are employed, the period between medical personnel attention is correspondingly longer.

(c) The filled syringes can be left in situ until the unit is changed.

The syringes can be pre-charged with small quantities of dry or liquid reagent which will stabilize the sample or protect the substance of interest.

Figure 2:
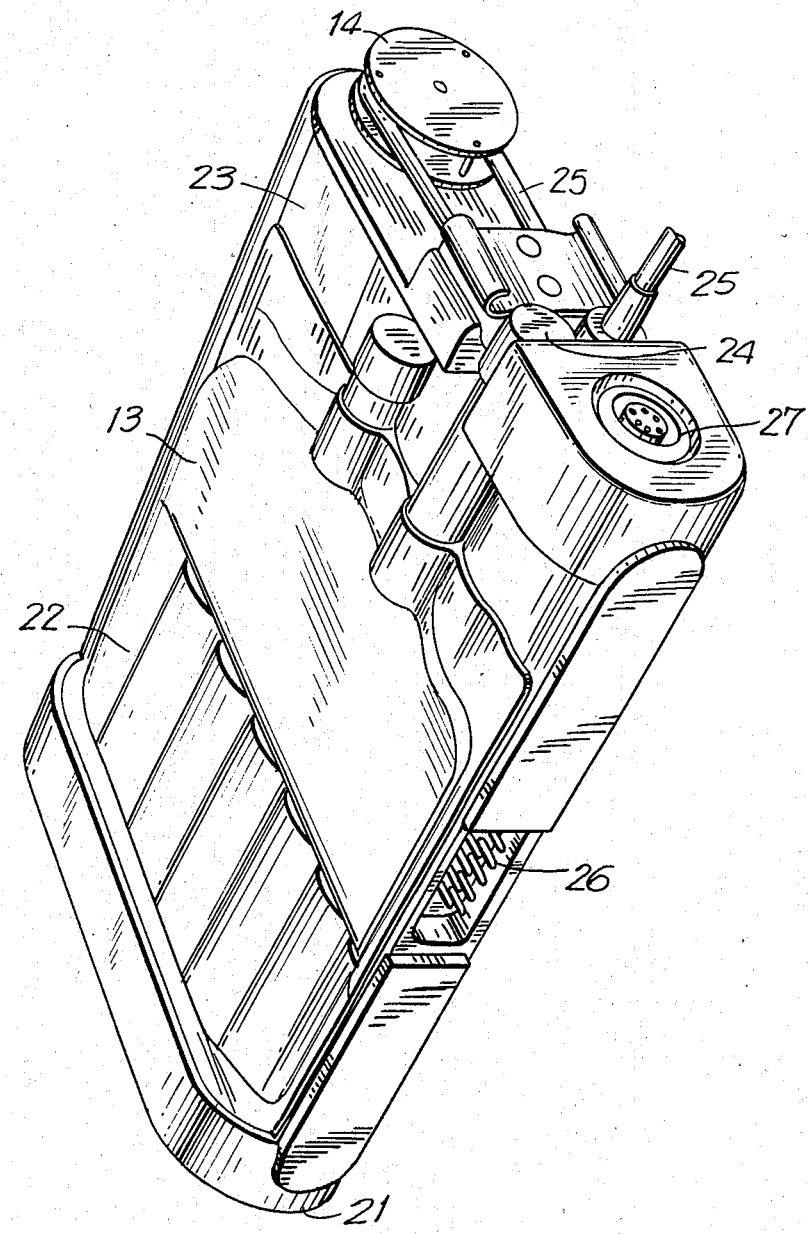
FIG. 2 is a perspective view, with parts cut away, of a pack to be carried by a patient.

Referring now in detail to FIG. 2, FIG. 2 illustrates a pack (designated generally 20) which contains certain of the parts referred to with reference to FIG. 1, but not the syringes which are separately located. In a relatively rigid casing 21 which is generally rectangular there are contained a power supply, here shown as a set of batteries 22, the reservoir 13 and pump 14 with a geared down driving motor 23 therefor. The reservoir may take the form of a flexible bag with a self-sealing cap 24 readily accessible under a removable cover (not shown) although other forms of containers may serve as reservoir 13. A tube 25 forming part of the pump 14, which is preferably of delta peristalsic type, is connected to the reservoir 13 and extends from the casing for connection to the syringe manifold 11. The casing 21 contains a controller, preferably a programmable controller such as a central processor unit and memory (not shown) settable on connection of a key pad to the microprocessor through connector 26. A syringe control cable (not shown) is connected to a socket 27, to supply power as required to a selected syringe.

The bag forming reservoir 13 may be a standard pediatric sachet of saline, with anticoagulant added through the self-sealing cap 24.

The motor M drives the peristaltic pump 14 through high reduction, and may be pulsed when extremely low speed is needed.

If required the syringes 10 (Syl-Sy7) may include one or more which, instead of aspirating to collect a sample, inject a liquid medication or the like into the manifold 11 so that when the manifold is flushed the liquid medication enters the patient. Treatment can be effected in this way. Alternatively all of the syringes may act to inject rather than aspirate in which case the invention may be employed for the programmed administration of medication. However, because of the problems of clotting in the taking of blood samples, this apparatus and method finds maximum utility in such use.

If desired, the method and apparatus described can be used to take or administer a single sample, for example at a time when medical attendance cannot be guaranteed. The apparatus does not need to be assembled into a pack for this purpose, and a single syringe may suffice.

When used as a blood sampler, the samples collected by the method and apparatus described herein need not be used exclusively or directly for the estimation of the effect of a drug. It can be equally instructive for the physician to obtain information about the concentration of a physiologically occurring substance, possibly one to be controlled by the administration of a drug, or even about the appearance or abundance of cellular constituents of the blood. For estimations of the highest accuracy, a known concentration of a marker substance can be incorporated in the flushing fluid and in any solution with which the syringes may be precharged. The concentration of this marker in the sample will then be a measure of the degree of dilution. The marker substance does not only have to be harmless, but must not occur in the body in significant amounts. There are dyes currently known and used in medical procedures which form satisfactory markers.

Figure 3:
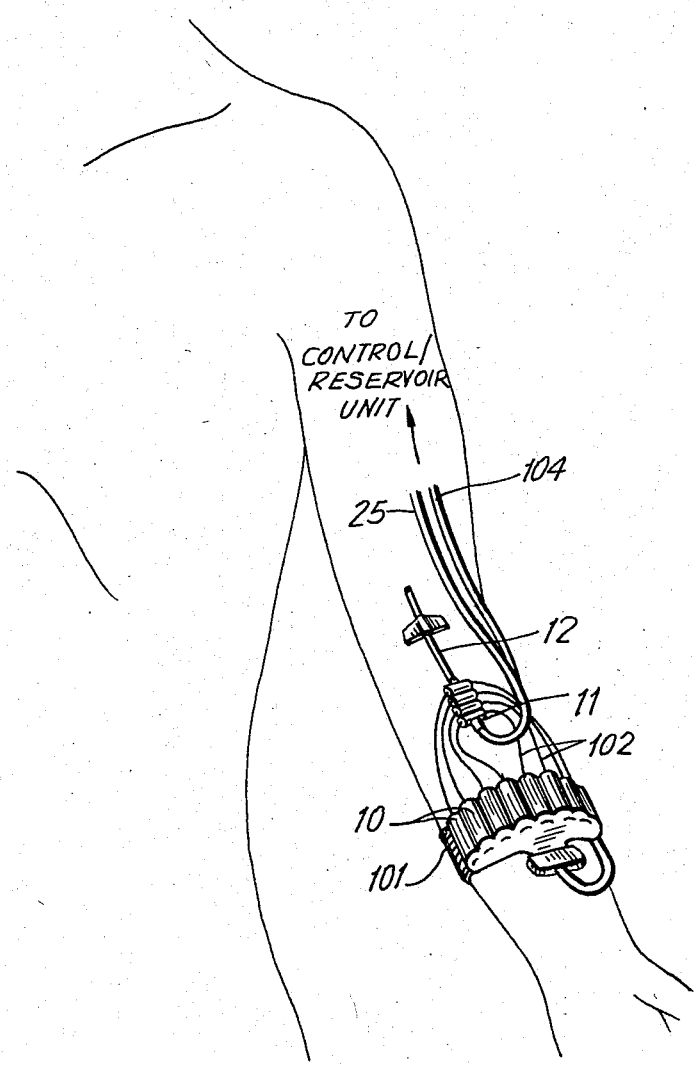

FIG. 3 shows how the parts of the apparatus can be located on a patient. Here, the syringes 10 are arranged as a bandolier 101 strapped to the patient's arm. Each syringe 10 is connected by a tube 102 of small diameter to the manifold 11, itself connected to a vein in the patient's arm by the cannula 12. The control unit reservoir and pump, as in FIG. 2, may be slung around the patient's body. The connecting tube 25 is shown in FIG. 3, and also a lead 104 providing the electrical connections for the syringes.

Other ways of supporting the apparatus on a patient are contemplated within the scope of this invention as defined by the claims.

While there has been described and illustrated a preferred embodiment of the present invention, it is apparent that numerous alterations, omissions and additions may be made without departing from the spirit and scope of the invention thereof.

What is claimed is:

1. A method of taking a plurality of blood samples from a blood vessel of a patient, using a like plurality of syringes therefor, said method comprising:
   (a) connecting a manifold to said blood vessel;
   (b) pumping at a slow rate anticoagulant through said manifold into said blood vessel;
   (c) interrupting pumping step (b) and then drawing from said patient into said manifold at a rapid rate blood for said sampling;
   (d) actuating a separate one of said plurality of syringes to remove from said manifold a sampling of blood;
   (e) discontinuing the actuation of each such syringe prior to the complete filling thereof with blood;
   (f) then flushing said manifold of blood by pumping therein at a rapid rate anticoagulant;
   (g) then reactuating the partially filled syringe to draw from said manifold anticoagulant; and
   (h) then returning to step (b) to operate another syringe to take another blood sample.

2. The method of claim 1 wherein the anticoagulant being pumped through said manifold into said blood vessel is pumped at a perfusion rate about two milliliters per hour.

3. A method according to claim 1 wherein the flushing of said manifold of blood by pumping therein at a rapid rate anticoagulant is carried out at a perfusion rate of about 20 milliliters per hour.

4. The method according to claim 3 wherein the anticoagulant is pumped through said manifold into said blood vessel during step (b) at a rate of about two milliliters per hour.

5. Apparatus for taking a blood sample comprising a manifold, means for connecting said manifold to a blood vessel of a patient, a syringe connected to said manifold for drawing a blood sample therefrom and fluid flow means operatively connected to the manifold for drawing blood into the manifold before sampling and for flushing said manifold afterwards with anticoagulant liquid, wherein said fluid flow means includes a reservoir for anticoagulant liquid and a reversible pump therefor, said apparatus further comprising control means for controlling the reversible pump and syringe so that before sampling blood with the syringe the reversible pump slowly pumps anticoagulant liquid into the patient, during sampling with the syringe the reversible pump rapidly pumps blood into the manifold, and after sampling blood with the syringe the reversible pump flushes the manifold rapidly with anticoagulant liquid.

6. The apparatus of claim 5 wherein the reversible pump is a peristaltic pump.

7. The apparatus of claim 5 wherein the reservoir has a self-sealing cap to permit refilling of the reservoir with anticoagulant liquid.

8. The apparatus of claim 7 wherein the reversible pump is a peristaltic pump.

9. Apparatus for taking a blood sample comprising a manifold which is adapted to receive a blood sampling syringe, means for connecting said manifold to a blood vessel of a patient, and fluid flow means operatively connected to the manifold for drawing blood into the manifold before sampling and for flushing said manifold afterwards with anticoagulant liquid, wherein said fluid flow means includes a reservoir for anticoagulant liquid and a reversible pump therefor, said apparatus further comprising control means for controlling the reversible pump and the syringe when a syringe is connected to the manifold so that before sampling blood with the syringe the reversible pump slowly pumps anticoagulant liquid into the patient, during sampling with the syringe the reversible pump rapidly pumps blood into the manifold, and after sampling blood with the syringe the reversible pump flushes the manifold rapidly with anticoagulant liquid.

10. The apparatus of claim 9 wherein the reversible pump is a peristaltic pump.

11. The apparatus of claim 9 wherein the reservoir has a self-sealing cap to permit refilling of the reservoir with anticoagulant liquid.

12. The apparatus of claim 11 wherein the reversible pump is a peristaltic pump.

13. A method of taking a blood sample comprising:
   (a) connecting a manifold to a blood vessel of a patient;
   (b) drawing blood from the patient into the manifold for sampling;
   (c) drawing a blood sample from said manifold with a syringe; and
   (d) flushing said manifold with anticoagulant after taking said blood sample;
   wherein, before blood sampling steps (b) and (c), anticoagulant liquid is pumped slowly into the patient; during step (b), the blood is drawn rapidly from the patient's blood vessel into the manifold; and wherein flushing is carried out immediately after blood sampling steps (b) and (c) by pumping at a rapid rate anticoagulant into the manifold to displace the blood therein, and after said flushing anticoagulant liquid is again pumped slowly into the patient.

14. A method as claimed in claim 13, wherein the syringe is activated twice for drawing a sample, once to collect the blood sample without completely filling the syringe with blood and a second time to aspirate anticoagulant liquid into the syringe.

15. Apparatus for taking blood samples from an ambulatory patient, said apparatus including housing means adapted to be carried on the patient, and further including: a manifold for connection with the patient, a plurality of syringes for successively drawing blood from said manifold, and fluid flow means for drawing blood into the manifold before sampling and for flushing it afterwards with anticoagulant liquid, wherein the fluid flow means includes a reservoir for anticoagulant liquid, a reversible pump therefor and control means for controlling the pump and syringes, so that the pump
   (a) between samples pumps anticoagulant liquid into the patients blood vessel,
   (b) pumps blood into the manifold for each successive sampling of blood, and
   (c) after each said sampling flushes the manifold with said anticoagulant liquid,
   wherein the control means further activates in sequence said syringes to collect samples from the manifold when blood is present therein, and wherein the manifold, syringes and fluid flow means are housed in said housing means.

16. Apparatus as claimed in claim 15, wherein after sampling by each such syringe, said last activated syringe is again activated to draw in anticoagulant liquid from the manifold.

17. Apparatus as claimed in claim 15 further comprising means for injecting fluid into said patient for treatment of the patient.

18. A method of taking a plurality of blood samples from an ambulatory patient using the apparatus of claim 15, comprising:
connecting the manifold to a blood vessel of said patient;
activating the series of syringes in succession at predetermined intervals of time to draw samples from the manifold; and
drawing blood from the patient into the manifold before sampling and flushing said manifold after blood sampling with anticoagulant liquid, wherein between samples anticoagulant liquid is pumped slowly into the vein; immediately before each sampling, blood is drawn rapidly from the vein into the manifold; and immediately after each sampling anticoagulant liquid is pumped into the manifold to pump the liquid in the manifold into the patient to displace the blood in the manifold with anticoagulant.

19. A method as claimed in claim 18, wherein after each sampling, the syringe last employed for blood sampling is again activated to draw in anticoagulant liquid from the manifold into the syringe.

20. A method as claimed in claim 18, further including the step of at least after one sampling injecting fluid for treatment of the patient into the liquid in the manifold prior to said liquid in the manifold being pumped into the patient.

* * * * *